(12) United States Patent
Van Dijk

(10) Patent No.: US 10,067,405 B2
(45) Date of Patent: Sep. 4, 2018

(54) OPTOELECTRONIC COMPONENT FOR GENERATING AND RADIATING A MICROWAVE-FREQUENCY SIGNAL

(71) Applicants: THALES, Courbevoie (FR); ALCATEL LUCENT, Boulogne Billancourt (FR)

(72) Inventor: Frédéric Van Dijk, Palaiseau (FR)

(73) Assignees: THALES, Courbevoie (FR); ALCATEL LUCENT, Boulogne Billancourt (FR)

( * ) Notice: Subject to any disclaimer, the term of this patent is extended or adjusted under 35 U.S.C. 154(b) by 0 days.

(21) Appl. No.: 15/537,344

(22) PCT Filed: Dec. 11, 2015

(86) PCT No.: PCT/EP2015/079354
§ 371 (c)(1),
(2) Date: Jun. 16, 2017

(87) PCT Pub. No.: WO2016/096633
PCT Pub. Date: Jun. 23, 2016

(65) Prior Publication Data
US 2017/0358901 A1 Dec. 14, 2017

(30) Foreign Application Priority Data
Dec. 17, 2014 (FR) .................................. 14 02880

(51) Int. Cl.
*G02F 1/35* (2006.01)
*H01S 5/0625* (2006.01)
(Continued)

(52) U.S. Cl.
CPC ....... *G02F 1/3534* (2013.01); *G01N 21/3581* (2013.01); *H01L 31/08* (2013.01); *H01S 5/026* (2013.01); *H01S 5/06258* (2013.01)

(58) Field of Classification Search
CPC .... G02F 1/3534; H01S 5/026; H01S 5/06258; H01L 31/08; G01N 21/3581
See application file for complete search history.

(56) References Cited

U.S. PATENT DOCUMENTS 3,517,330 A * 6/1970 Doyle .................. H01S 3/1396
372/32
6,967,347 B2 * 11/2005 Estes ..................... B82Y 10/00
257/25
(Continued)

FOREIGN PATENT DOCUMENTS

JP 2003004532 A * 1/2003
WO 2006/011668 A1 2/2006

OTHER PUBLICATIONS

Stephane Demiguel et al., "Very High-Responsivity Evanescently Coupled Photodiodes Integrating a Short Planar Multimode Waveguide for High-Speed Applications," IEEE Photonics Technology Letters, vol. 15, No. 12, Dec. 2003, pp. 1761-1763.
(Continued)

*Primary Examiner* — Daniel Petkovsek
(74) *Attorney, Agent, or Firm* — Baker & Hostetler LLP

(57) ABSTRACT

An optoelectronic component for generating and radiating an electromagnetic signal exhibiting a frequency lying between 30 GHz and 10 THz referred to as a microwave frequency, comprises: a planar guide configured to confine and propagate freely in a plane XY a first and a second optical wave exhibiting an optical frequency difference, referred to as a heterodyne beat, equal to the microwave frequency, a system for injecting the optical waves into the planar guide, a photo-mixer coupled to the planar guide to generate, on the basis of the first optical wave and of the second optical wave, a signal exhibiting the microwave frequency, the photo-mixer having an elongated shape exhibiting along an axis Y a large dimension greater than or equal to half the wavelength of the signal, the injection system configured so that the optical waves overlap in the (Continued)

planar guide and are coupled with the photo-mixer over a length along the axis Y at least equal to half the wavelength of the signal, the photo-mixer thus being able to radiate the signal.

17 Claims, 13 Drawing Sheets

(51) Int. Cl.
  *H01S 5/026* (2006.01)
  *G01N 21/3581* (2014.01)
  *H01L 31/08* (2006.01)

(56) References Cited

U.S. PATENT DOCUMENTS

| | | | | |
|---|---|---|---|---|
| 7,723,708 B2* | 5/2010 | Ouchi | ................ | G01N 21/3581 250/250 |
| 9,377,668 B2* | 6/2016 | Brun | ...................... | G02B 6/102 |
| 2012/0147907 A1 | 6/2012 | Kim et al. | | |

OTHER PUBLICATIONS

Frederic Van Dijk et al., "Integrated InP Heterodyne Millimeter Wave Transmitter," IEEE Photonics Technology Letters, vol. 26, No. 10, May 15, 2014, pp. 965-968.

Andreas Beling et al., "High-Speed Photodiodes," IEEE Journal of Selected Topics in Quantum Electronics, vol. 20, No. 6, Nov./Dec. 2014.

A. Stoehr et al., "Optical Heterodyne Millimeter-Wave Generation Using 1.55-um Traveling-Wave Photodetectors," IEEE Transactions on Microwave Theory and Techniques, vol. 49, No. 10, Oct. 1, 2001, pp. 1926-1933, XP001108245.

E. Rouvalis et al., "High-speed photodiodes for InP-based photonic integrated circuits," Optics Express, vol. 20, No. 8, Apr. 9, 2012, pp. 9172, XP055081154.

* cited by examiner

OPTOELECTRONIC COMPONENT FOR GENERATING AND RADIATING A MICROWAVE-FREQUENCY SIGNAL

CROSS-REFERENCE TO RELATED APPLICATIONS

This application is a National Stage of International patent application PCT/EP2015/079354, filed on Dec. 1, 2015, which claims priority to foreign French patent application No. FR 1402880, filed on Dec. 17, 2014, the disclosures of which are incorporated by reference in their entirety.

FIELD OF THE INVENTION

The invention relates to optoelectronic components, and more particularly to integrated components having the function of generating and radiating an electromagnetic signal exhibiting a frequency lying between 30 GHz and 10 THz referred to as a microwave frequency hereinafter in the document, on the basis of optical waves exhibiting a wavelength of between 400 nm and 10 μm.

BACKGROUND

The generation of microwave-frequency signals of millimetric wave type (RF radio wave of frequency between 30 GHz and 300 GHz) and of TeraHertz type (frequency between 100 GHz and 10 THz) exhibits numerous applications in the fields of detection, spectroscopy and high-bitrate wireless data transmission. In the latter field, the higher the support frequency, the more significant the bitrate that can be transported. By way of example, for a 1-GHz carrier, a maximum bitrate of 1 Gbit/s is obtained, whilst with a carrier of 1 THz, bitrates of 10 to 20 Gbit/s are possible, hence the interest in developing components capable of emitting in this range of frequencies with sufficient power.

A first solution according to the prior art is a component 100 able to emit a signal S of microwave frequency F, illustrated in FIGS. 1a-1b (FIG. 1a perspective view and FIG. 1b view from above). This unitary photodiode 100 comprises a planar guide 10 in which two optical waves propagate, a wave O1 of wavelength λ1 and a wave O2 of wavelength λ2, and an associated photo-mixer 11 of small size. λ1 and λ2 are such that they exhibit a heterodyne beat, that is to say that the modulus of the difference f1−f2 of the associated optical frequencies f1 and f2 is equal to a frequency F in the microwave-frequency domain:

$$f1 = C/\lambda 1$$

$$f2 = C/\lambda 2$$

$$F = |f1 - f2| \text{ of the order of a TeraHz.}$$

The optical waves are coupled to the photo-mixer 11 by evanescent coupling in such a way that the latter generates a wave at the frequency F.

The photodiode 100 also comprises a metal antenna 12, exhibiting a bowknot shape, coupled to the photo-mixer 11, and which radiates an electromagnetic signal S of frequency F into space.

The photo-mixer length $l_{10}$ is typically from 10 to 20 μm since it is necessary to limit the parasitic capacitance that the device would exhibit and which would strongly attenuate the signal detected at the frequency F. Moreover, a lengthening would not make it possible to increase the absorbed power, the major part of the light being absorbed in the first 10 microns of the component.

The width $L_{10}$ is dimensioned to be of the order of magnitude of the optical wavelengths, typically 2 to 3 times greater, but not more.

Indeed, $L_{10}$ must remain small enough for the component to operate correctly beyond 30 GHz. When $L_{10}$ becomes too large, the transport of the signal at the semi-conductor (photo-mixer 11)/metal (antenna 12) interface is degraded by the presence of parasitic capacitances (capacitive effects and transit time effects) the effect of which is to attenuate the photogenerated signal S of frequency F.

The dimensional limitation of $L_{10}$ has the drawback of limiting the power that can be radiated.

Moreover, the small dimension of the component 100 compels the use of an antenna 12 in order to accommodate the size of the RF mode of the signal S.

A second solution according to the prior art is a system 200 able to emit a signal S of microwave frequency F, based on an integration of planar photodiodes arranged as a 2D matrix or of an emitter of large surface area in the form of a large-size photodiode, such as illustrated in FIG. 2. The optical waves O1 and O2 are directly incident on a side of the component PM which radiates the signal of frequency F on the opposite side.

This solution exhibits low effectiveness of coupling because the photo-mixer PM consists of a layer of small thickness, thus limiting the interaction between the light and the photo-mixer. Moreover, to polarize each photo-mixer of the matrix, it is necessary to produce opaque electrodes which reduce the area of interaction between the light and the photo-mixers.

Its implementation with discrete optical elements for shaping the signals O1 and O2 renders the system 200 bulky. Moreover, this system does not make it possible to integrate on the same wafer other functions which interact with light such as amplification, modulation of amplitude or of phase. Furthermore, 2D matrices do not make it possible to localize the illumination in the zones where photo-detection is desired in an effective manner, thereby limiting the high-frequency power generated/incident optical power efficiency.

When it is sought to introduce a scan of a radio wave in the millimetric range, current solutions exhibit several drawbacks. A solution based on discrete optical components is bulky and the signal emitted exhibits strong divergence. An alternative solution based on mechanical elements is also bulky, and comprises a mobile element which is not compatible with all systems.

An aim of the present invention is to alleviate the aforementioned drawbacks and more particularly to produce an integrated optoelectronic component able to generate and radiate a microwave-frequency signal (also referred to as a high-frequency signal) without any antenna.

SUMMARY OF THE INVENTION

The subject of the present invention is an optoelectronic component for generating and radiating an electromagnetic signal exhibiting a frequency lying between 30 GHz and 10 THz referred to as a microwave frequency, comprising:

a planar guide configured to confine and propagate freely in a plane XY a first and a second optical wave exhibiting an optical frequency difference, referred to as a heterodyne beat, equal to said microwave frequency, a system for injecting said optical waves into said planar guide, a photo-mixer coupled to said planar guide so as to generate, on the basis of the first optical wave and of the second optical wave, a signal exhibiting said microwave frequency, said photo-mixer having an elongated shape exhibiting along an axis Y a large dimension greater than or equal to half the wavelength of the signal, said injection system being configured so that said optical waves overlap in said planar guide and are coupled with the photo-mixer over a length along the axis Y at least equal to half the wavelength of said signal, the photo-mixer thus being able to radiate said signal (S).

Advantageously, said planar guide comprises a propagation layer between two confinement layers.

Advantageously, the photo-mixer is deposited on a confinement layer and the coupling is performed by evanescent waves.

According to one embodiment, the planar guide is configured to confine optical waves each exhibiting a wavelength of close to 1.5 µm.

According to a variant, the planar guide comprises an amplifying part able to amplify said first and second optical waves.

According to a variant, the injection system is configured so that the injected optical waves exhibit strong divergence.

Advantageously, said injection system comprises at least one so-called monodimensional guide configured to confine the optical waves in such a way that said waves propagate along their respective directions of propagation.

Preferentially, the monodimensional guide consists of a prolongation of the planar guide comprising a strip-shaped confinement layer.

According to one embodiment, the injection system comprises at least one optical fiber.

According to one embodiment, the injection system comprises a single injection device. Preferentially, said single injection device is configured to inject the first and second optical waves in such a way that said waves propagate along a direction of propagation substantially equal to a direction X perpendicular to the axis Y.

According to another embodiment, said injection system comprises a first injection device configured to inject the first optical wave in such a way that said first wave propagates along a first direction of propagation lying in the plane XY, and a second injection device configured to inject the second optical wave in such a way that said second wave propagates along a second direction of propagation lying in the plane XY and different from the first direction of propagation.

Advantageously, a single one of said first and second injection devices exhibits a direction of propagation perpendicular to said axis Y.

According to one embodiment, the planar guide furthermore comprises at least one deflector situated on the optical path of one of the optical waves and configured to deflect said optical wave in such a way as to deviate it by a chosen angle of optical deviation, so that the signal radiated by said photo-mixer is able to be deviated according to an angle of deviation dependent on said angle of optical deviation.

Preferentially, the deflector is an electro-optical modulator configured to modify the refractive index of a portion of the propagation layer, said portion exhibiting a prismatic shape in the plane XY.

According to one embodiment, said deflector is a phase modulator comprising a plurality of independently controlled discrete phase-shifters.

Preferentially, each discrete phase-shifter is an electro-optical modulator configured to modify the refractive index of a portion of the propagation layer (Cp).

BRIEF DESCRIPTION OF THE DRAWINGS

Other characteristics, aims and advantages of the present invention will become apparent on reading the detailed description which follows and with regard to the appended drawings given by way of nonlimiting examples and in which:

FIG. 1a illustrates a perspective view and FIG. 1b illustrates a view from above, FIG. 2 already cited illustrates a 2D system for generating a microwave-frequency signal according to the prior art, FIG. 3a illustrates a view from above and FIG. 3b illustrates a profile view, FIG. 4 describes an exemplary planar guide, FIG. 5 describes a first variant of the component according to the invention integrating an amplification function, FIG. 7a illustrates a view from above and FIG. 7b illustrates a profile view, FIG. 9a illustrates a view from above and FIG. 9b illustrates a profile view.

DETAILED DESCRIPTION OF THE INVENTION

Figure 3:
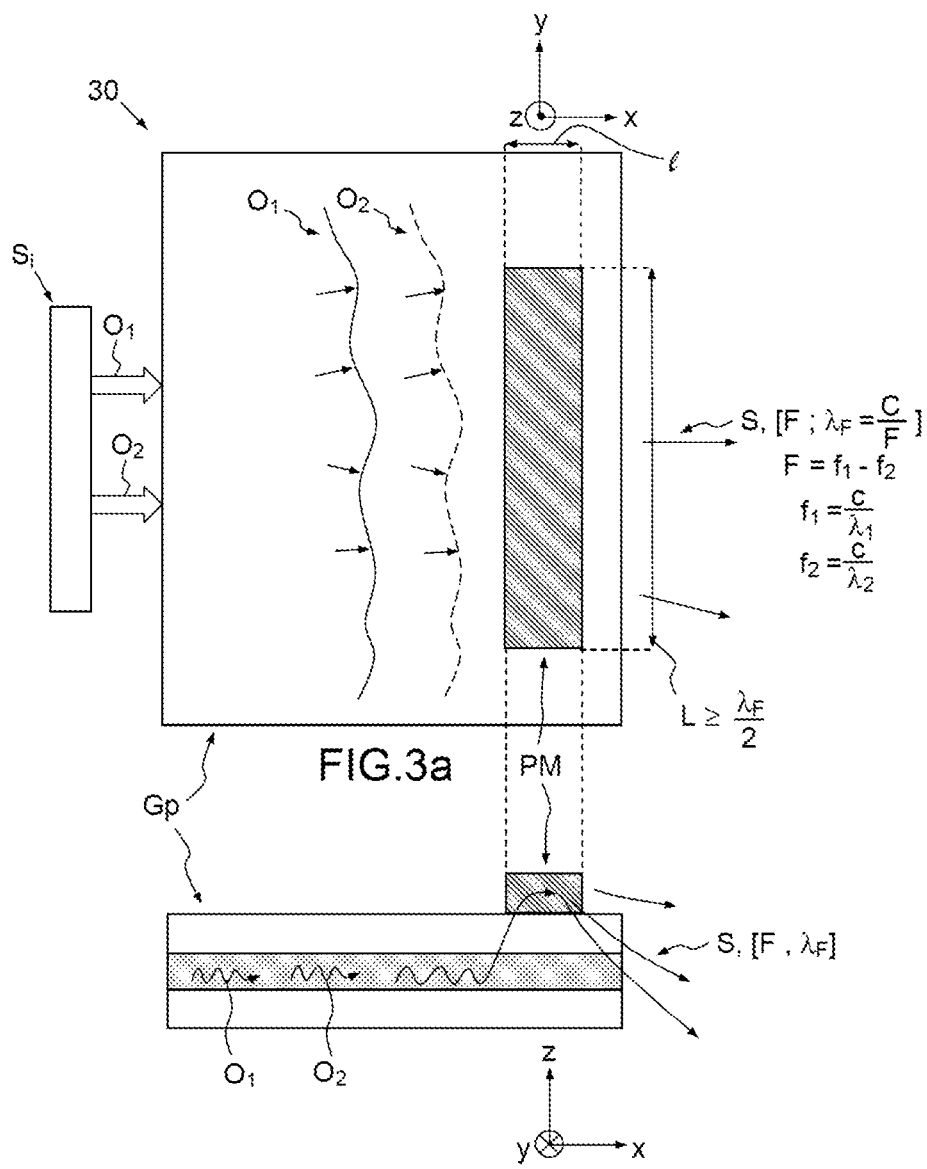
FIGS. 3a-3b illustrate an optoelectronic component according to the invention.

FIGS. 3a-3b illustrate an optoelectronic component 30 according to the invention. FIG. 3a illustrates a view from above and FIG. 3b illustrates a profile view.

This component is able to generate and radiate an electromagnetic signal S exhibiting a frequency F lying between 30 GHz and 10 THz referred to as a microwave frequency. Preferentially, the microwave frequency emitted lies between 100 GHz and 2 THz.

This frequency span covers the millimetric RF frequencies and the THz frequencies.

The component 30 comprises a planar guide Gp configured to confine and propagate freely in a plane XY a first optical wave O1 of wavelength $\lambda 1$ and of optical frequency $f1=C/\lambda 1$ and a second optical wave O2 of wavelength $\lambda 2$ and of optical frequency $f2=C/\lambda 2$, these two waves exhibiting an optical frequency difference $f1-f2$, referred to as a heterodyne beat, equal to a microwave frequency F.

$$|f1-f2|=F$$

The optical waves typically exhibit a wavelength of between 400 nm and 10 µm, and preferentially between 1.2 µm and 7 µm.

The wavelengths $\lambda 1$ and $\lambda 2$ are very close. For example for F=1 THz and $\lambda 1$=1.50 µm, we have $\lambda 2$=1.508 µm.

The component 30 also comprises an injection system Si for injecting optical waves O1, O2 into the planar guide Gp. Various injection configurations compatible with the invention are described further on.

Finally, the component 30 also comprises a photo-mixer PM coupled to the planar guide Gp so as to generate, on the basis of the first optical wave O1 and of the second optical wave O2, a signal S exhibiting the microwave frequency F.

The photo-mixer PM according to the invention has an elongated shape exhibiting along an axis Y a large dimension L greater than or equal to $\lambda_F/2$, with $\lambda_F$ the wavelength of the signal S of frequency F:

$$L \geq \lambda_F/2 \text{ with } \lambda_F = C/F$$

Moreover, the injection system Si is configured so that the optical waves O1 and O2 overlap in the planar guide Gp and are coupled with the photo-mixer PM over a length along the axis Y at least equal to half the wavelength $\lambda_F$ of the signal S.

The divergence of a beam, if the latter is assumed to be of Gaussian type, takes place with a total angle which will be 150° if the dimension of the radiating element is $\lambda_F/2$. If the dimension of the radiating element is still smaller, the directivity of the emitter will be very degraded and it will not be possible for the emitted beam to be used effectively. Thus, a radiation at the frequency F with an acceptable divergence requires a radiating element of a dimension at least equal to $\lambda_F/2$.

The overlapping of the waves over a distance of at least $\lambda_F/2$ at the level of the photo-mixer PM and its elongated shape along Y thus render it able to radiate the signal S in space in a direction of propagation X substantially perpendicular to Y, without requiring an additional antenna. The elongated photo-mixer PM receives light which propagates in the planar guide Gp on one side and re-emits the signal S arising from the photo-mixing on the other side.

The large dimension L of the photo-mixer PM allows a radiation which is hardly divergent in the plane XY. Moreover, the increase in the size of the PM with respect to that of the photo-mixer of a unitary photodiode, such as described in FIGS. 1a-1b, also makes it possible to distribute the power over the whole dimension L and thus to increase the optical power that can be coupled without destruction, leading to a more powerful signal S being radiated.

Figure 1A:
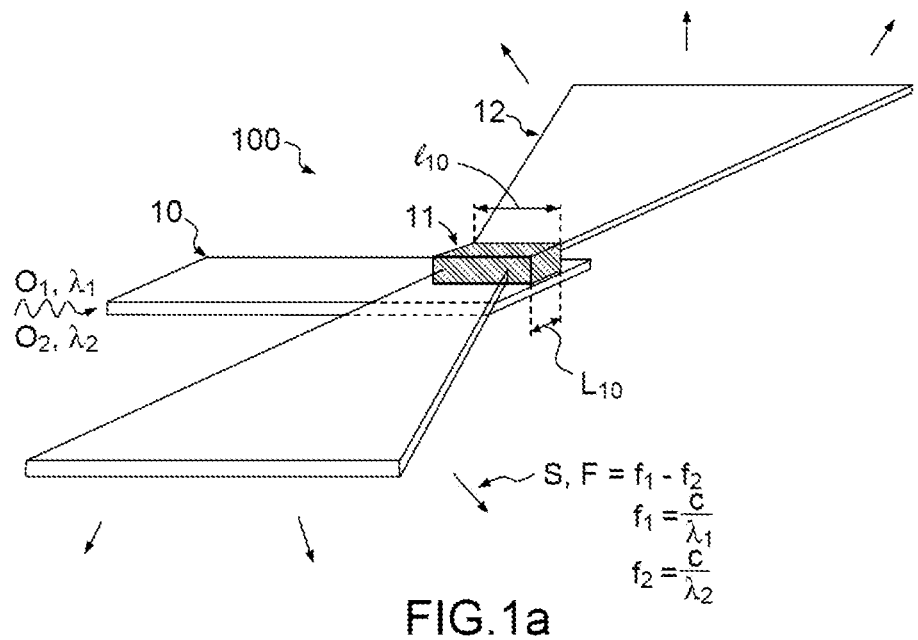
FIGS. 1a-1b already cited illustrate a unitary component for generating a microwave-frequency signal according to the prior art.
Figure 1B:
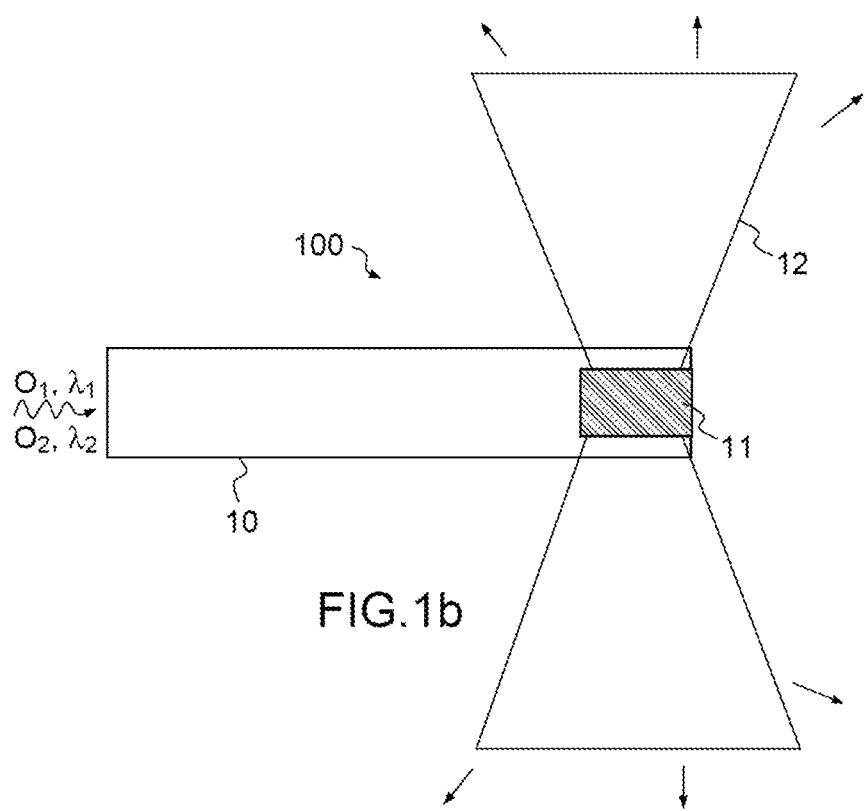
Figure 2:
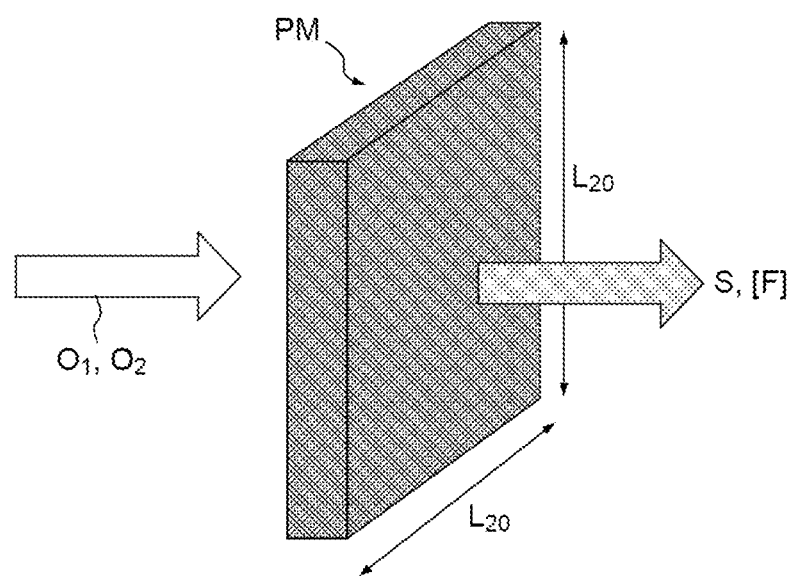

The small dimension I is for example of the same order of magnitude as the dimension $I_{10}$ of the unitary photodiode of FIGS. 1a-1b.

The signal radiated by the photo-mixing exhibits a frequency F lying in a frequency range [30 GHz, 10 THz], preferentially [100 GHz, 2 THz]. For example, the corresponding wavelengths $\lambda_F$ for the latter band lie between 40 µm and 900 µm, in a GaAs or GaInAsP photo-mixer material.

The fact that the coupling of the optical waves with the elongated photo-mixer PM is achieved through a planar guide Gp confers on the component 30 an integrated structure of high efficiency, rendering it quite compact, and allowing the planar guide Gp to be supplemented with additional functions described further on allowing processing of the light propagating in the component.

Figure 4:
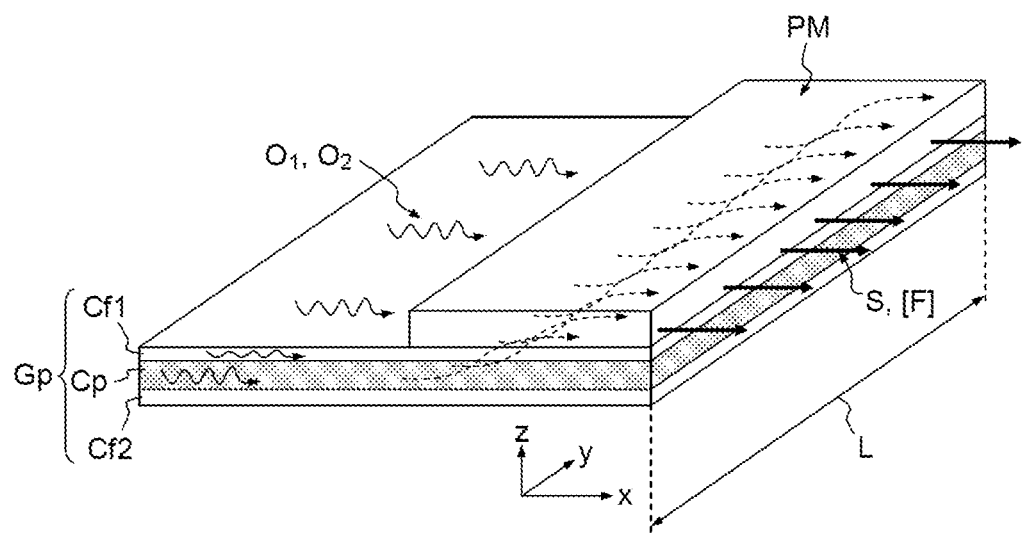

Preferentially, the planar guide Gp comprises a propagation layer Cp between two confinement layers Cf1, Cf2, such as is illustrated in FIG. 4.

By way of illustrative example, the planar guide Gp is configured to confine optical waves each exhibiting a wavelength of close to 1.5 µm, which is obtained with the aid of well-known DFB or DBR sources based on GaInAsP on InP.

The propagation layer Cp comprises a GaInAsP layer and each confinement layer Cf1, Cf2 comprises an InP layer.

Preferentially, the photo-mixer PM is deposited on a confinement layer and the coupling is performed through evanescent waves.

According to another variant, the coupling is of "end-to-end" type, the photo-mixer PM being placed directly facing the propagation layer. For the previous illustrative example, typically the photo-mixer comprises GaInAsP.

Figure 5:
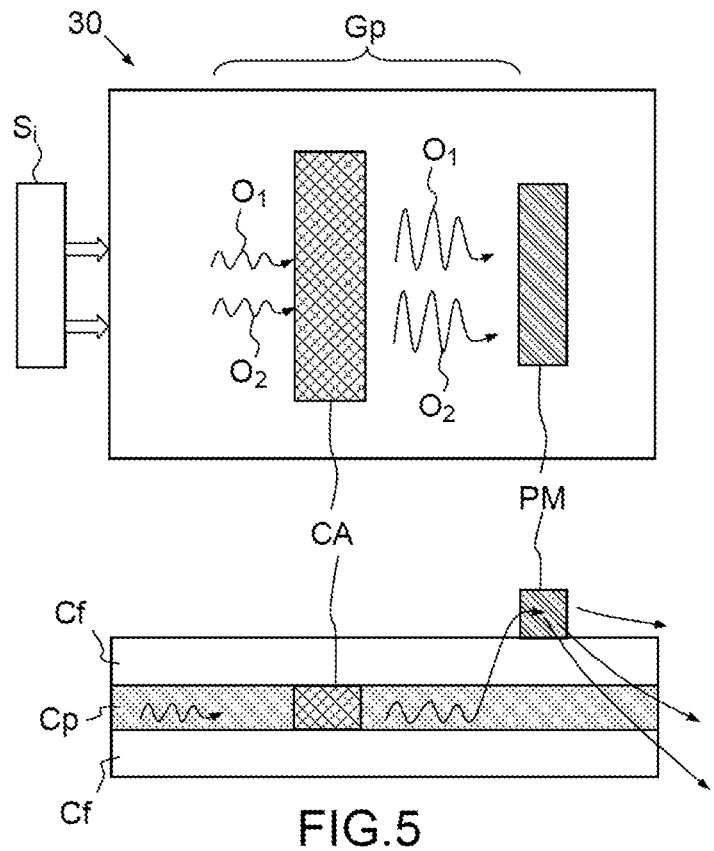

According to a first variant, the integrated character of the structure of the component 30 allows the addition of an amplification function inside the planar guide, as illustrated in FIG. 5 (FIG. 5a represents the view from above and FIG. 5b represents the profile view). For example, the planar guide Gp comprises an amplifying part CA produced in the propagation layer Cp and able to amplify the optical waves O1 and O2. Thus, the available optical power is increased by the amplifying part CA, thereby enabling the component 30 to generate and radiate a signal S exhibiting likewise increased microwave-frequency power.

Figure 6:
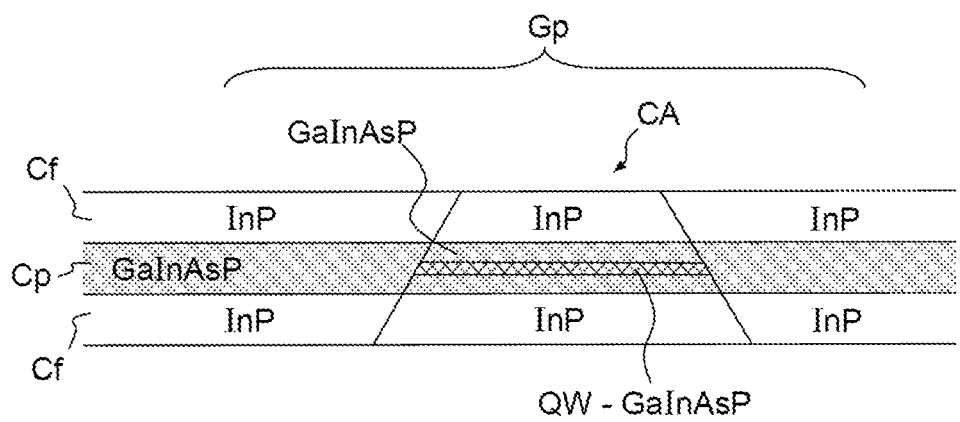
FIG. 6 illustrates an exemplary planar guide of the component according to the invention with integrated amplifier.

For the previous illustrative example, the amplifying layer CA preferentially comprises a GaInAsP layer comprising GaInAsP quantum wells QW, such as is illustrated in FIG. 6.

There may be a single or several quantum wells. They consist of barriers made of GaInAsP and wells also made of GaInAsP. The composition of the barriers and of the wells differs so as to create a potential well allowing the generation of light when a current is applied.

We shall now give nonlimiting examples of configurations of the injection system Si.

In order to generate optical waves O1 and O2 which exhibit a sufficient dimension at the level of the photo-mixer PM, a variant is that the injection system Si is configured so that the injected optical waves exhibit strong divergence.

For example, concentrated beams forming two pseudo sources of very small dimension, almost point sources, are coupled in Gp.

Figure 7A:
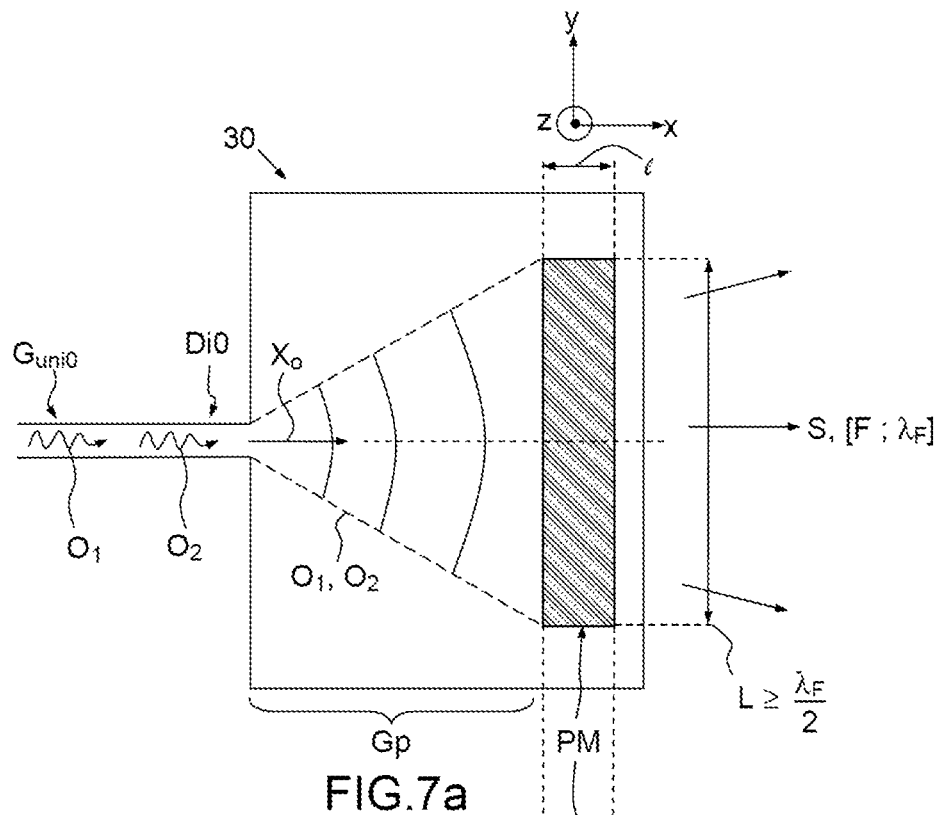
FIGS. 7a-7b illustrate a first embodiment of the injection system of the component according to the invention comprising a single injection device.
Figure 7B:
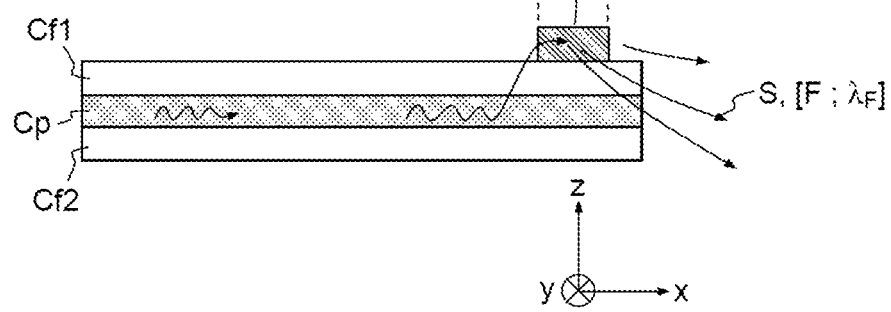

According to a first embodiment illustrated in FIGS. 7a-7b, the injection system Si comprises a single injection device Di0 common to the two waves O1 and O2. FIG. 7a represents the view from above and FIG. 7b represents the profile view. The waves O1 and O2 are then collinear, thereby guaranteeing optimum overlapping and culminating in a simplified component.

Preferentially, the single injection device Di0 is configured to inject the optical waves O1, O2 in such a way that they propagate in the planar guide in a direction of propagation substantially equal to a direction X perpendicular to the axis Y. This configuration is relatively simple since it requires the implementation of a single optical coupling to inject O1 and O2.

A first variant, also illustrated in FIGS. 7a-7b, for obtaining waves O1 and O2 with strong divergence in Gp, is that the injection device Di0 comprises a so-called monodimensional guide Guni0 configured to confine the optical waves O1, O2 in such a way that these waves propagate along their common direction of propagation X0 lying in the plane XY. Each wave confined in the monodimensional guide will see its divergence increase strongly when it penetrates into the planar guide, on account of the widening of the propagation zone. Each wave thus propagates "freely" in the plane XY about a direction XO equal to the direction of the monodimensional guide.

An optimal configuration is a guide Guni perpendicular to Y and along an axis X0 passing through the middle of PM.

Figure 8:
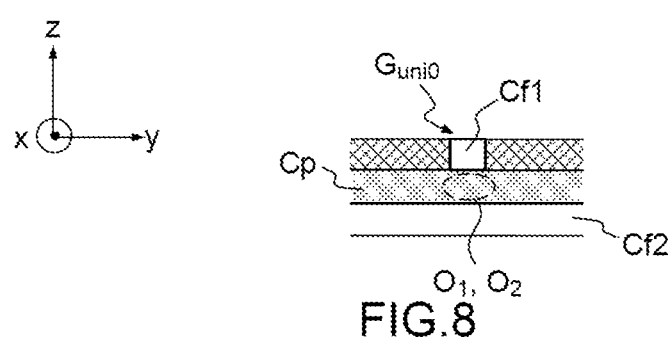
FIG. 8 illustrates a single injection device obtained by prolongation of the planar guide viewed in section.

Preferentially, the monodimensional guide Guni0 consists of a prolongation of the planar guide Gp on the side on which the light arrives and comprises a strip-shaped confinement layer. The optical waves propagating in the propagation layer Cp are then confined along the direction of the strip, as illustrated in FIG. 8.

The guide Guni0 can be obtained by locally removing the material used to form Cf1, so as to form a strip along the axis x. Knowing that the refractive index of the material used for Cp is greater than the refractive indices of the material used for Cf1 and Cf2, the optical waves O1 and O2 are confined along the axis y to form a single-mode waveguide.

A second variant for obtaining waves O1 and O2 with strong divergence in Gp is an injection device Di0 comprising a single fiber terminating in a tip coupled to the planar guide Gp.

Figure 9:
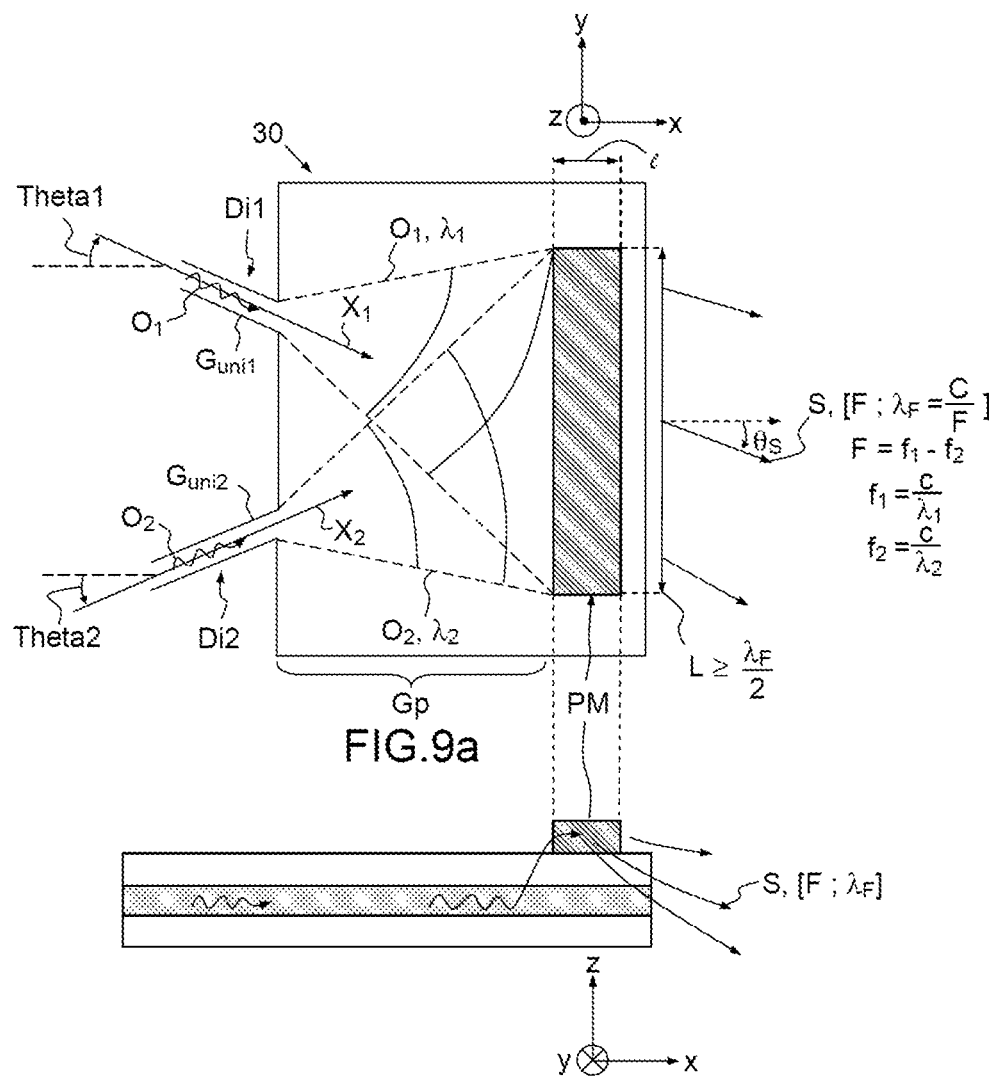
FIGS. 9a-9b illustrate a second embodiment of the injection system of the component according to the invention comprising two injection devices, one for each optical wave.

According to a second embodiment illustrated in FIGS. 9a-9b, the injection system Si comprises a first injection device Di1 configured to inject the first optical wave O1 in such a way that it propagates along a first direction of propagation X1 lying in the plane XY, and a second injection device Di2 configured to inject the second optical wave O2 in such a way that it propagates along a second direction of propagation X2 lying in the plane XY and different from the first direction of propagation X1. FIG. 9a represents the view from above and FIG. 9b represents the profile view.

The direction X1 exhibits an angle of theta1 with respect to the axis x. The direction X2 exhibits an angle theta2 with respect to the axis x.

The signal S is then generated according to an angle Θs corresponding to the angle between the direction of propagation Xs of the signal S and the axis x in the plane xy.

In this configuration, Θs is deduced from the following relation:

$$\Theta s = \sin^{-1}\{\lambda_F*[(\sin(theta1)/\lambda_1)+(\sin(theta2)/\lambda_2)]\}$$

This configuration allows independent processing of the two waves O1 and O2, which are no longer collinear in this case. The propagation axes X1 and X2 and the divergence of the optical waves are configured so that the waves O1 and O2 overlap over a dimension greater than or equal to $\lambda_F/2$ at the level of the photo-mixer PM.

Figure 10:
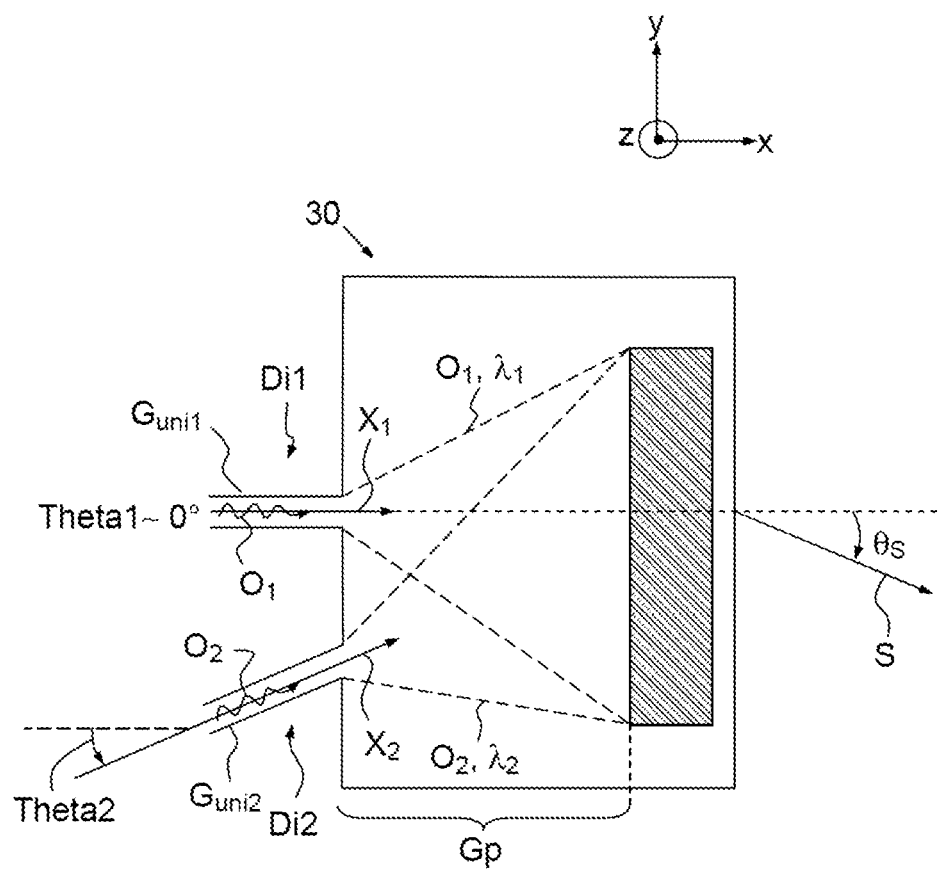
FIG. 10 illustrates a preferred mode of the component according to the invention in which a device for injecting an optical wave is such that the optical wave propagates perpendicularly to the axis y.

According to a preferred mode such as illustrated in FIG. 10, a single one of the devices, for example the first device Di1, is disposed in such a way that the wave O1 follows a direction of propagation X1 substantially perpendicular to the axis y (theta1~0°) and the second injection device Di2 is disposed in such a way that the wave O2 follows a direction X2.

In this configuration, Θs is deduced from the following relation:

$$\Theta s = \sin^{-1}\{[\lambda_F/\lambda_2]*\sin(theta2)\}$$

For example, for a 1-THz signal S, having a wavelength $\lambda_F$=C/F=300 µm with an optical signal O2 at a wavelength $\lambda_2$ of 1.5 µm with an angle theta1=0° and theta2=0.2°, the angle Θs equals 44°.

It is noted that a very small difference theta1−theta2 gives rise to a significant deviation of the microwave-frequency signal.

For the variant with monodimensional guide, each injection device Di1 and Di2 comprises respectively a guide Guni1, Guni2 oriented along the directions X1, X2. The wave O1 is injected via Guni1 and the wave O2 is injected via Guni2.

For the variant with optical fibers, the first injection device Di1 comprises a first optical fiber and the second injection device Di2 comprises a second optical fiber. The wave O1 is injected via the first fiber and the wave O2 is injected via the second fiber.

According to a second variant, the integrated character of the structure of the component 30 allows the addition of a function of deviation of at least one optical wave by spatial phase shifting.

Figure 11:
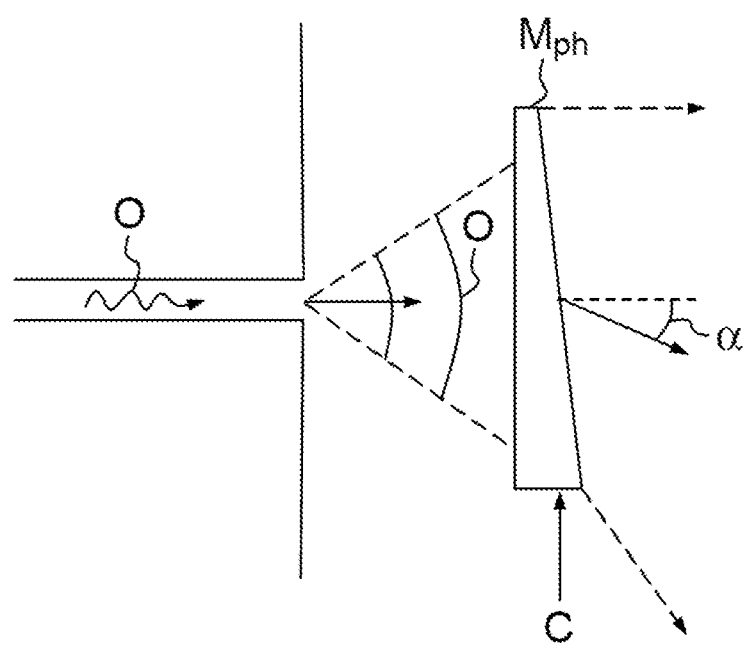
FIG. 11 illustrates the principle of deviation of an optical wave in the planar guide.

The principle of the deviation of a wave O with strong divergence propagating in a planar guide by phase shifting is illustrated in FIG. 11. The deflector Mph is configured to vary the optical phase shift spatially, continuously or discretely so as to effect a deviation by a chosen angle α of the direction of propagation of the wave O, according to a known principle.

The deflector is for example controlled with the aid of an electrical control C.

Figure 12:
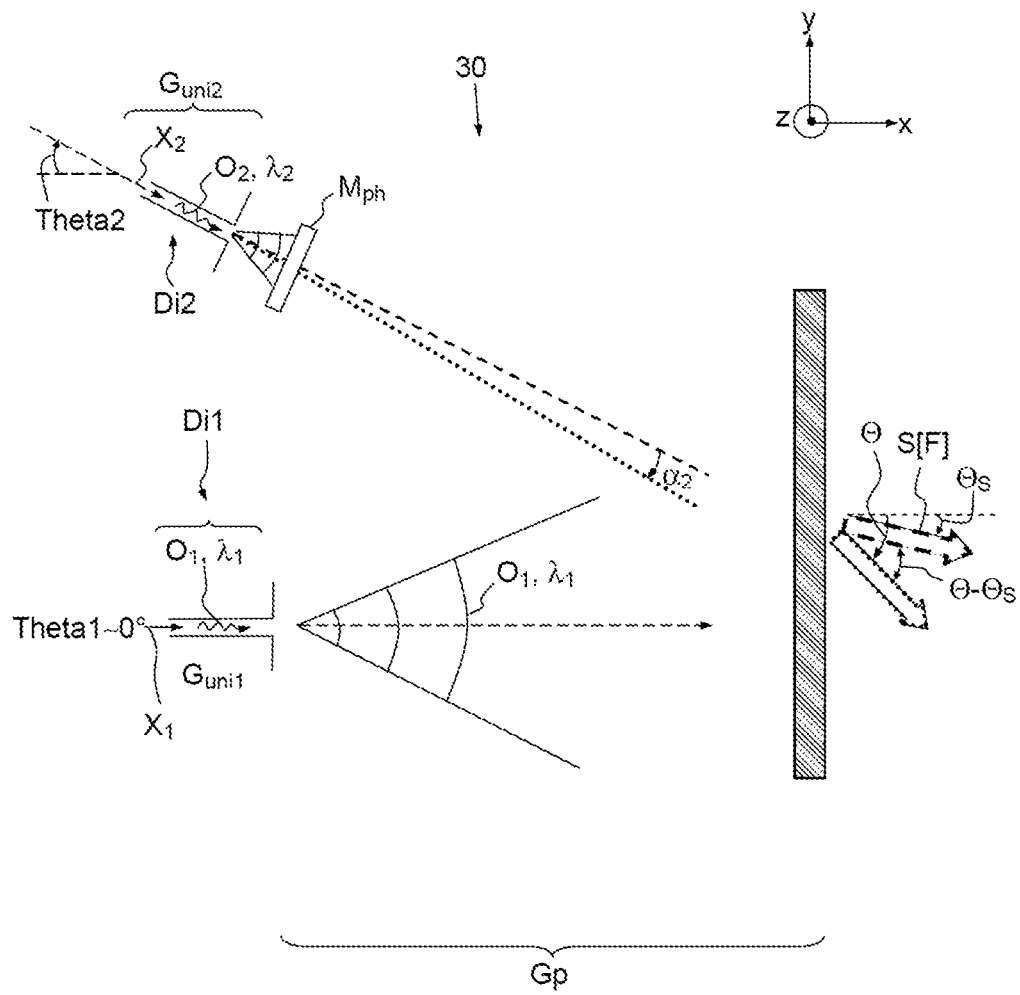
FIG. 12 illustrates a component according to the invention according to the preferred mode and able to deflect the microwave frequency wave.

This function is applied to the component 30 according to the invention such as is illustrated in FIG. 12 in the preferred configuration illustrated in FIG. 10.

In this embodiment, the planar guide Gp of the component 30 according to the invention furthermore comprises a deflector $M_{Ph}$ situated for example on the optical path of the optical wave O2 exhibiting a direction of propagation according to a non-zero angle theta2, and configured to deflect the second optical wave O2 in such a way as to deviate it with respect to the initial direction of propagation theta2 by a chosen angle α2 of optical deviation.

At the level of the photo-mixer PM, this variation of direction of propagation α2 is echoed at the level of the radiation of the microwave-frequency signal S, for which the direction of radiation Xs making an angle Θs (that is to say the direction of corresponding pointing of the maximum radiated energy) is also deviated by an angle of deviation Θ−Θs dependent on the angle of optical deviation α2. In this configuration, the angle Θ that the microwave frequency wave makes with the axis x is deduced from the following relation:

$$\Theta = \sin^{-1}\{\lambda_F(\sin(theta2+\alpha 2)/\lambda_2)\}$$

Thus, on departure the microwave frequency wave S exhibits an angle Θs, which is modified into an angle Θ.

For example, for a 1-THz signal S having a wavelength $\lambda_F$=C/F=300 µm and obtained with an optical signal O2 at a wavelength $\lambda_2$ of 1.5 µm with an angle theta1=0° and theta2=0.2°, the angle Θs will equal 44°.

For a deflection of the signal O2 of 0.05 achieved with the deflector $M_{Ph}$, the angle Θ is 61°. The signal S is thus deflected by 17°.

Due to the elongated geometry of the photo-mixer, the deviated signal S preserves the weak divergence in the plane XY.

With a controllable deflector making it possible to modify the value of α2, it is possible to carry out an angular scan of the signal S.

Figures 13A, 13B:
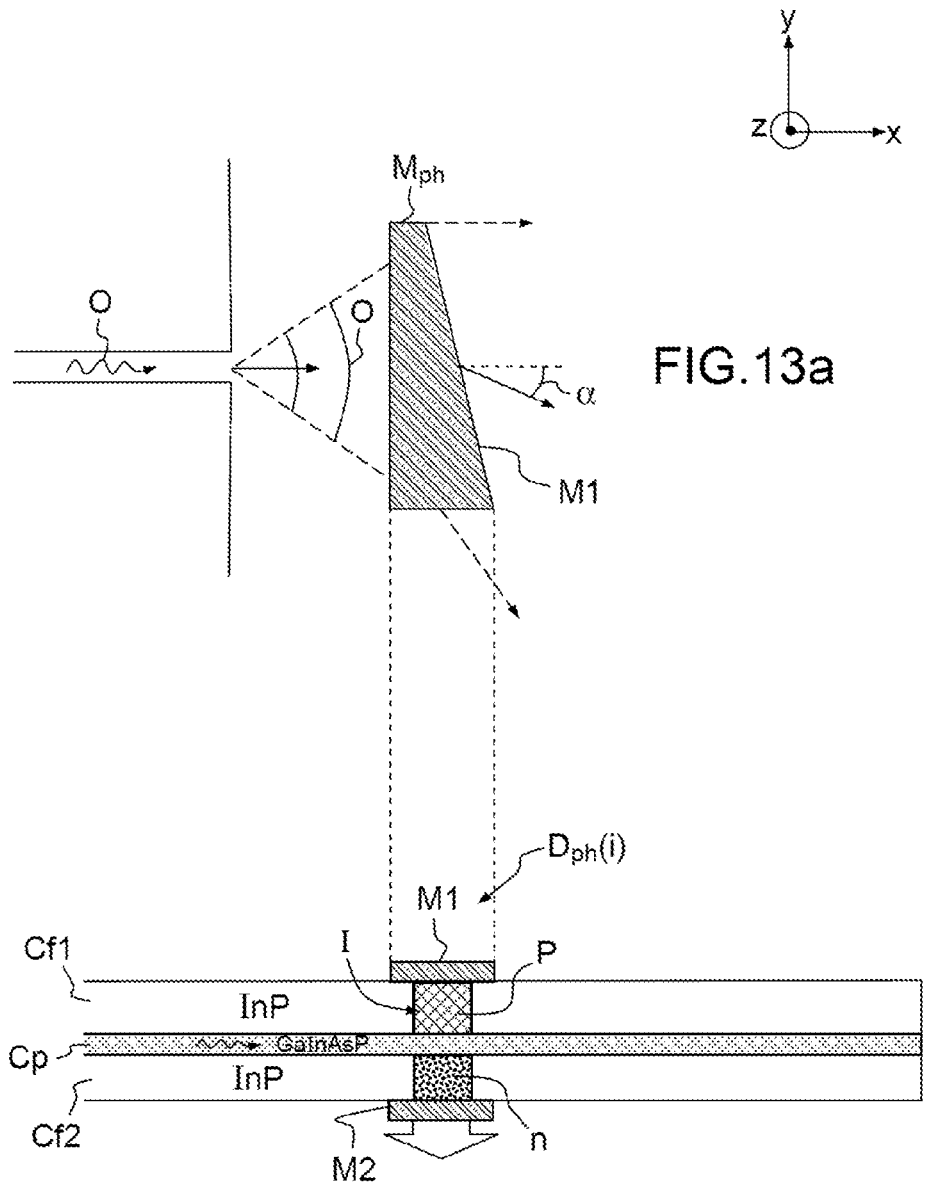
FIG. 13a illustrates an exemplary continuous phase-shifter viewed from above and FIG. 13b illustrates this phase-shifter viewed in section.

An exemplary electro-optical deflector $M_{ph}$ is illustrated in FIG. 13a (view from above) and FIG. 13b (sectional view) for a planar guide comprising a propagation layer Cp made of GaInAsP and two confinement layers Cf1 Cf2 made of InP.

A metallic layer M1 disposed on the layer Cf1 delimits $M_{ph}$. A zone of the layer Cf1 under the metallic layer M is p-doped while the zone of the layer Cf2 on the other side of the propagation layer Cp is n-doped. Another metallic layer M2 is placed in contact with the layer Cf2. The electrical continuity of the layer Cf2 makes it possible to inject a current between M1 and M2.

It is thus possible to inject a current I into the propagation layer in the zone localized under the metallic layer, the effect of which is to locally modify the refractive index as a function of the value of I. If no current is applied, the refractive index seen by the optical signal O is the same in the zones which surround $M_{ph}$ and inside $M_{ph}$. The beam O is then not deviated by $M_{ph}$. If a current I is applied, the refractive index seen by the optical signal O is different in the zones which surround $M_{ph}$ from that inside $M_{ph}$.

The deflector $M_{ph}$ is thus an electro-optical modulator configured to modify the refractive index of a portion of the propagation layer Cp. When the portion exhibits a prismatic shape in the plane XY, and for a higher index inside $M_{ph}$ in the propagation layer than outside, the optical wave O, on account of the Fresnel laws, is deviated in the same manner as in the case of a prism.

Figure 14:
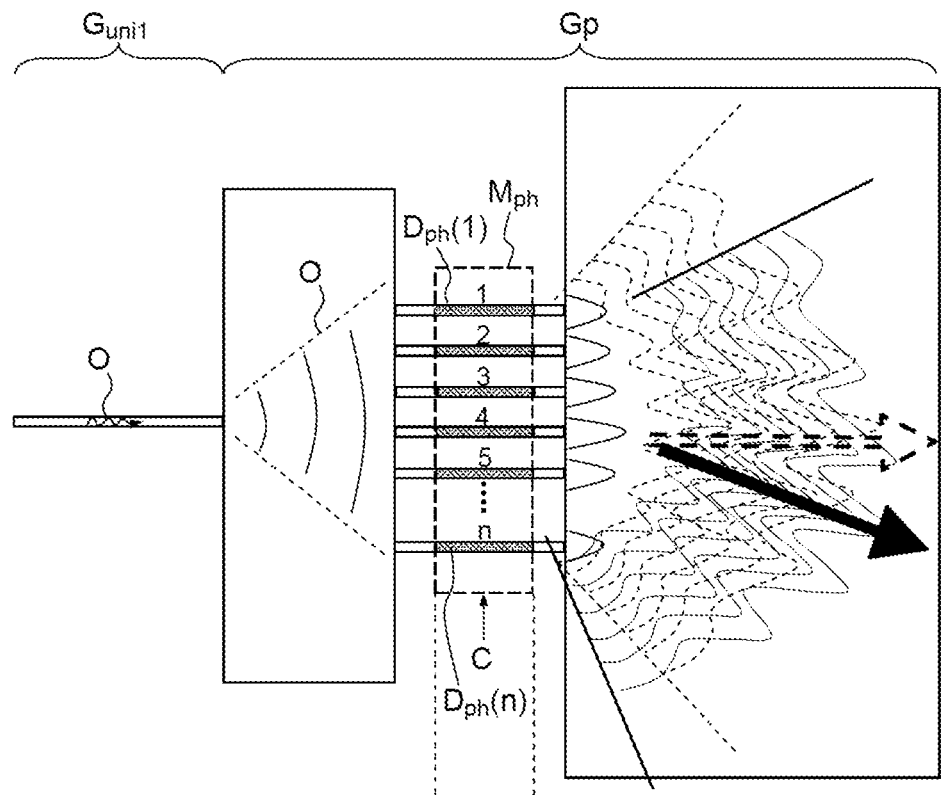
FIG. 14 illustrates a phase modulator comprising a plurality of discrete phase-shifters.

According to a second example, the deflector is a phase modulator $M_{ph}$ comprising a plurality of i independently controlled discrete phase-shifters $D_{ph}(1), \ldots D_{ph}(n)$. The principle of this discrete phase-shifter is illustrated in FIG. 14 for an optical wave O.

The optical wave, propagated in a first zone of "free" propagation of the planar guide, is distributed over n channels. An optical phase-shifter Dph(i) per channel varies the optical phase shift of channel i independently of the other channels. The waves arising from the channels then propagate in a second "free" propagation zone in the planar guide Gp. In this second zone a wavefront forms whose direction depends on the phase shifts applied by means of the phase-shifters. The phase front of the optical wave is therefore controlled via the phase-shifter. For a determined phase law, a global deviation of the wavefront with respect to the incident wavefront is obtained.

The phase-shifter operates for example in an electro-optical manner, that is to say that an electrical control signal modifies the refractive index in a channel comprising for example a portion of the propagation layer.

Figure 15:
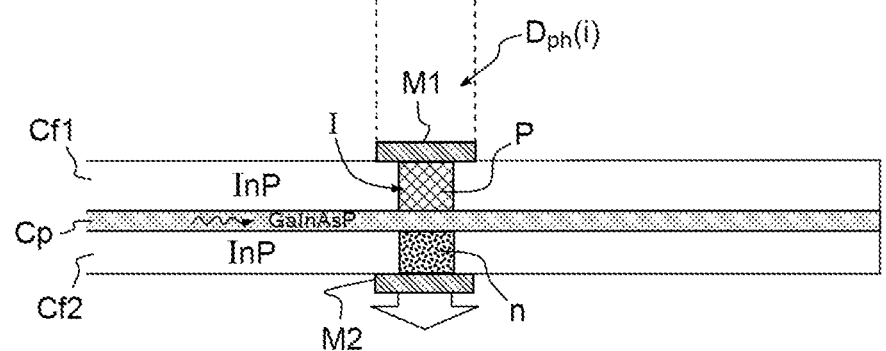
FIG. 15 illustrates an exemplary discrete electro-optical phase-shifter.

An electro-optical phase-shifter Dph(i) is illustrated in FIG. 15 for a planar guide comprising a propagation layer Cp made of GaInAsP and two confinement layers Cf1 Cf2 made of InP. It operates in the same manner as the phase-shifter of FIG. 13b. A metallic layer M1 is disposed on the layer Cf1. A zone of the layer Cf1 under the metallic layer M is p-doped while the zone of the layer Cf2 on the other side of the propagation layer Cp is n-doped. Another metallic layer M2 is placed in contact with the layer Cf2. The electrical continuity of the layer Cf2 makes it possible to inject a current between M1 and M2. The effect of injecting a current I into the propagation layer is to locally modify the refractive index as a function of the value of I.

It is of course possible to integrate, in addition to the deflector, electrically powered optical amplifiers so as to modify the optical power.

The optical amplifiers are for example positioned in each channel, thus enabling the optical power to be made uniform between the various channels.

Figure 16:
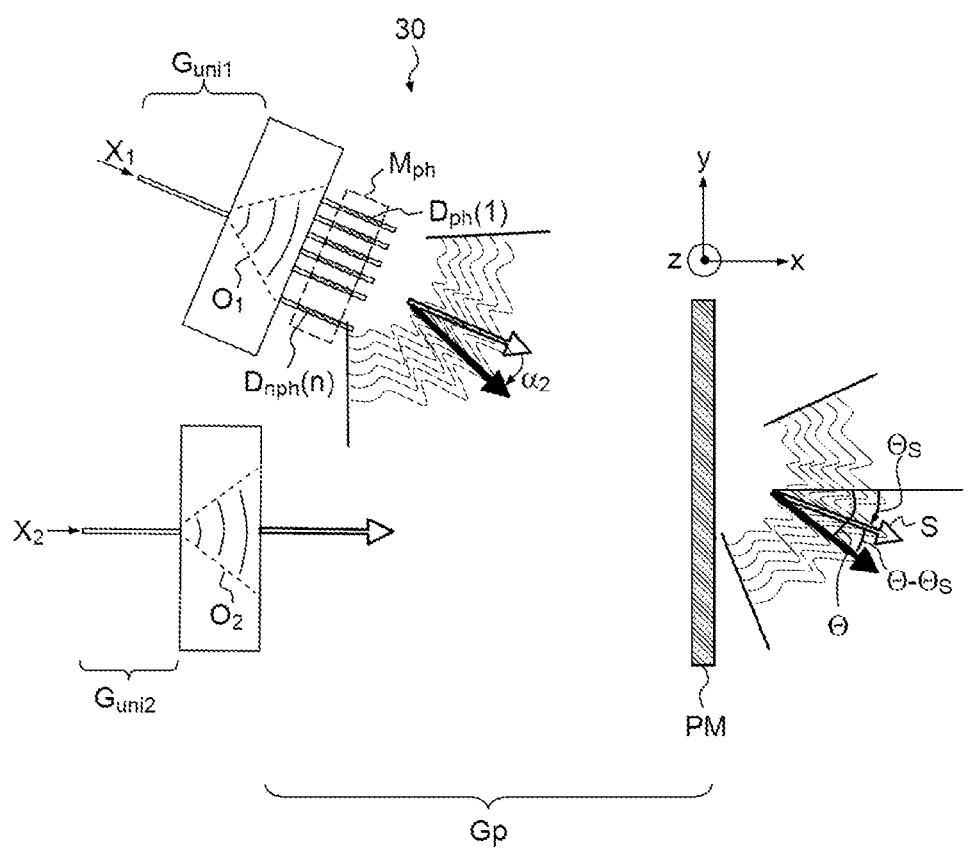
FIG. 16 illustrates a component according to the invention according to the preferred mode able to deflect the microwave frequency wave with the aid of a phase modulator.

FIG. 16 illustrates a component according to the invention whose planar guide Gp comprises an electro-optical phase modulator $M_{Ph}$ such as described hereinabove on the optical path of the wave exhibiting a non-zero angle Theta1, here O1.

The signal S radiated by the photo-mixer PM is able to be deviated (that is to say the direction of corresponding pointing of the maximum radiated energy) according to an angle of deviation Θ dependent on theta1, theta2 and α2. The deviation with respect to the initial angle Θs is (Θ-Θs).

Thus, the integrated character of the component 30 according to the invention makes it possible to profit from the lengthening of the photo-mixer PM so as to facilitate the implementation of amplification and scanning functions, forming a photonic integrated circuit carrying out an angular scan of a high-frequency F signal S.

The invention claimed is:

1. An optoelectronic component or generating and radiating an electromagnetic signal exhibiting a frequency between 30 GHz and 10 THz, being a microwave frequency, comprising:
    a planar guide configured to confine and propagate freely in an X-Y plane a first optical wave and a second optical wave exhibiting an optical frequency difference, being a heterodyne beat, equal to said microwave frequency,
    an injection system for injecting said first optical wave and said second optical wave into said planar guide,
    a photo-mixer coupled to said planar guide so as to generate, on the basis of the first optical wave and of the second optical wave, a signal exhibiting said microwave frequency,
    said photo-mixer having an elongated shape exhibiting along a Y-axis a large dimension greater than or equal to half the wavelength of said signal,
    said injection system being configured so that said first optical wave and said second optical wave overlap in said planar guide and are coupled with the photo-mixer over a length along the Y-axis at least equal to half the wavelength of said signal, the photo-mixer thus being able to radiate said signal.

2. The optoelectronic component as claimed in claim 1, wherein said planar guide comprises a propagation layer between two confinement layers.

3. The optoelectronic component as claimed in claim 2, wherein the photo-mixer is deposited on a confinement layer and said coupling with the photo-mixer is performed by evanescent waves.

4. The optoelectronic component as claimed in claim 1, wherein the planar guide is configured to confine optical waves each exhibiting a wavelength of approximately 1.5 µm.

5. The optoelectronic component as claimed in claim 1, wherein said planar guide comprises an amplifying part able to amplify said first optical wave and second optical wave.

6. The optoelectronic component as claimed in claim 1, wherein the injection system is configured so that injected optical waves exhibit strong divergence.

7. The optoelectronic component as claimed in claim 1, wherein said injection system comprises at least one monodimensional guide configured to confine optical waves in such a way that said first optical wave and said second optical wave propagate along their respective directions of propagation.

8. The optoelectronic component as claimed in claim 7, wherein the monodimensional guide consists of a prolongation of the planar guide comprising a strip-shaped confinement layer.

9. The optoelectronic component as claimed in claim 1, wherein the injection system comprises at least one optical fiber.

10. The optoelectronic component as claimed in claim 1, wherein the injection system comprises a single injection device.

11. The optoelectronic component as claimed in claim 10, wherein said single injection device is configured to inject the first optical wave and second optical wave in such a way that said first optical wave and said second optical wave propagate along a direction of propagation substantially equal to an X-axis perpendicular to the Y-axis.

12. The optoelectronic component as claimed in claim 1, wherein said injection system comprises a first injection device configured to inject the first optical wave in such a way that said first optical wave propagates along a first direction of propagation lying in the X-Y plane, and a second injection device configured to inject the second optical wave in such a way that said second optical wave propagates along a second direction of propagation lying in the X-Y plane and different from the first direction of propagation.

13. The optoelectronic component as claimed in claim 12, wherein a single one of said first and second injection devices exhibits a direction of propagation perpendicular to said Y-axis.

14. The optoelectronic component as claimed in claim 12 wherein the planar guide furthermore comprises at least one deflector situated on the optical path of one of the first optical wave and second optical wave and configured to deflect said one of the first optical wave and second optical wave in such a way as to deviate it by a chosen angle of optical deviation,
   so that the signal radiated by said photo-mixer is able to be deviated according to an angle of deviation dependent on said chosen angle of optical deviation.

15. The optoelectronic component as claimed in claim 14, wherein said deflector is an electro-optical modulator configured to modify the refractive index of a portion of the propagation layer, said portion exhibiting a prismatic shape in the X-Y plane.

16. The optoelectronic component as claimed in claim 14, wherein said deflector is a phase modulator comprising a plurality of independently controlled discrete phase-shifters.

17. The optoelectronic component as claimed in claim 16, wherein each discrete phase-shifter is an electro-optical modulator configured to modify the refractive index of a portion of the propagation layer.

* * * * *